United States Patent
Di-Benedetto et al.

(10) Patent No.: US 6,420,481 B2
(45) Date of Patent: Jul. 16, 2002

(54) IMPACT MODIFIED POLYAMIDE COMPOSITIONS

(75) Inventors: Silvia Di-Benedetto, Geneva (CH); Edmund A. Flexman, Wilmington, DE (US)

(73) Assignee: E. I. du Pont de Nemours and Comapny, Wilmington, DE (US)

( * ) Notice: Subject to any disclaimer, the term of this patent is extended or adjusted under 35 U.S.C. 154(b) by 0 days.

(21) Appl. No.: 09/783,832

(22) Filed: Feb. 15, 2001

Related U.S. Application Data (63) Continuation-in-part of application No. 09/765,749, filed on Jan. 19, 2001, now abandoned.
(60) Provisional application No. 60/181,594, filed on Feb. 10, 2000, and provisional application No. 60/177,274, filed on Jan. 21, 2000.

(51) Int. Cl.[7] .............................................. C08L 77/00
(52) U.S. Cl. ........................................ 525/66; 525/179
(58) Field of Search ..................................... 525/66, 179

(56) References Cited

U.S. PATENT DOCUMENTS 4,485,214 A  11/1984  Ochiai et al.

FOREIGN PATENT DOCUMENTS

| GB | 1552352 | 9/1979 |
|----|---------|--------|
| WO | WO 98/38227 | 9/1998 |
| WO | WO 01/53415 | 7/2001 |

*Primary Examiner*—Ana Woodward (57) ABSTRACT

A multiphase polymer composition having increased impact resistance at low temperatures, includes a blend of an ionomer dispersed in nylon 6, a polyamide other than nylon 6, and a composition that includes EP or EPDM grafted with 0.05 to 3 weight percent of a carboxylic acid or any anhydride thereof. The ionomer is formed from a partially neutralized acid copolymer precursor, the acid copolymer precursor having polymerized in-chain units derived from the monomers comprising: (a) ethylene, (b) 2 to 25 weight percent of (meth)acrylic acid, (c) 0.1 to 15 weight percent of a dicarboxylic acid monomer, (d) 0–40 weight percent of a C1–C8-alkyl alkyl acrylate, the ionomer being formed by neutralization of from about 5 to 90 percent of the total number of carboxylic acid units in the copolymer with metal ions. The (meth)acrylic acid and dicarboxylic acid monomer is from 4 to 26 weight percent of the acid copolymer precursor, and the total comonomer content preferably does not exceed 50 weight percent of the acid copolymer precursor. Preferably, the ionomer has a melt index of from 0.01 to 100 grams/10 minutes, and the ratio of the number of moles of metal ions in the ionomer to the number of moles of the carboxylic acid or any anhydride thereof in the grafted EP or EPDM is greater than 1.0.

13 Claims, 5 Drawing Sheets

IMPACT MODIFIED POLYAMIDE COMPOSITIONS

This application is a continuation-in-part of U.S. application Ser. No. 09/765,749, filed Jan. 19, 2001, now abandoned, and from Provisional Application No. 60/181,594, filed Feb. 10, 2000 and Provisional Applicaiton No. 60/177,274, filed Jan. 21, 2000.

BACKGROUND OF THE INVENTION

1. Field of the Invention

This invention relates to the field of toughened polyamides, and more particularly to the field of polyamides that are toughened by the addition of tougheners such as ionomers and ethylene copolymers.

2. Description of the Related Art

Improvement of impact strength, or toughness, of polyamide resins has long been of interest. Resistance to shattering or brittle breaking on impact of polyamide molded articles is a desirable feature of any molded article. Any tendency to break on impact in a brittle fashion (rather than ductile fashion) is a significant limitation on the usefulness of such articles. By "ductile" is meant that sharp cracks in the molded resin are not initiated, or if initiated do not tend to propagate, from the area of impact. Breaks in ductile materials are characterized more by tearing with a large volume of adjacent material yielding at the edge of the crack or tearing rather than a sharp, clean break with little molecular displacement. A resin having good ductility is one that is resistant to crack propagation caused by impact.

A variety of additives have been added to polyamide resins to improve strength and ductility. For example, U.S. Pat. No. 4,174,358 issued Nov. 13, 1979 to Epstein, describes improving impact strength and ductility by adding a selected random copolymer which adheres to the polyamide. U.S. Pat. No. 4,594,386 issued Jun. 10, 1986 to Olivier, describes improving impact strength and toughness of polyamide resins by blending polyamide resin with maleic anhydride grafted EPM rubber of low molecular weight. U.S. Pat. No. 4,346,194 issued Aug. 24, 1982 to Roura, describes a polyamide molding material having good impact strength at low temperatures, e.g., 0° C.; the polyamide molding material comprises a nylon 6/66 blend and a toughening copolymer that is an adduct of a polymer of ethylene, at least one C3–C6 alpha-olefin and at least one non-conjugated diene, with an unsaturated compound containing carboxyl or carboxyl derivatives.

The inverse relationship between percent neutralization and ionic polymer flow rate, such as might be measured by melt index, i.e., M.I., is well known. This inverse relationship can present a processing problem in cases where it may be desired to process a highly neutralized ionomer resin that contains even moderate levels of methacrylic acid. While it can be inferred that a higher degree of neutralization of acid groups in the resin can lead to greater toughening, ultimate flow rates at the highest levels of neutralization, as measured by M.I., approach a "no flow" condition, i.e., the resin blend becomes intractable. In U.S. Pat. No. 5,688,868 issued Nov. 18, 1997 to Fish, there is disclosed a process for preparing blends of polyamide and ionic copolymers which have very high degrees of neutralization by adding metal ions to the blend in situ in amount which exceed that needed to neutralize 100% of the acid molecules present-in the blend without incurring a "no flow" condition.

In addition, U.S. Pat. Nos. 4,346,194 and 4,478,978 to Roura disclose toughened blends of nylon 6,6 and nylon 6.

Although the previously known combinations impart improved toughness to polyamide resins, it has now been found that certain novel compositions provide further improvements in polyamide resin toughness at very low temperatures, including temperatures less than about −30° C. This invention is directed to a polyamide molding blend suitable for making molded articles for use in applications requiring toughness at very low temperatures.

The present invention is directed to the discovery that the toughness of a polyamide that includes an EP or EPDM grafted with 0.05 to 3 weight percent of a carboxylic acid or an anhydride thereof can be unexpectedly increased by the addition of a particular ionomer at least partially dispersed in nylon 6, provided that the number of moles of selected metal ions in the ionomer is greater than or equal to the number of moles of the carboxylic acid in the grafted EP or EPDM.

SUMMARY OF THE INVENTION

The present invention relates to a multiphase polymer composition having increased impact resistance at low temperatures, that includes a blend of (1) an ionomer at least partially dispersed in nylon 6, the ionomer being formed from a partially neutralized ethylene acid interpolymer precursor, the ethylene acid interpolymer precursor having polymerized in-chain units derived from the monomers comprising:
  (a) ethylene,
  (b) 2 to 25 weight percent of an acid selected from the group of acrylic acid, methacrylic acid, and mixtures thereof,
  (c) 0.1 to 15 weight percent of a dicarboxylic acid monomer selected from the group consisting of maleic acid, fumaric acid, itaconic acid, maleic anhydride, itaconic anhydride, a $C_1$–$C_4$-alkyl half ester of maleic acid, and a mixture of these dicarboxylic acid monomers,
  (d) 0–40 weight percent of a C1–C8-alkyl alkyl acrylate,
the ionomer being formed by neutralization of from about 5 to 90 percent of the total number of carboxylic acid units in the copolymer with metal ions selected from the group of zinc, magnesium, manganese and mixtures thereof, alone or in combination with sodium or lithium ions,
with the proviso that the total of acrylic acid, methacrylic acid, and dicarboxylic acid monomer is from 4 to 26 weight percent of the acid copolymer precursor,
the ionomer having a melt index of from 0.01 to 100 grams/10 minutes; and (2) a polyamide other than nylon 6, and (3) a composition that includes an elastomer selected from the group of EP, EPDM and styrenic thermoplastic elastomer, which elastomer is grafted with 0.05 to 3 weight percent of a carboxylic acid or any anhydride thereof;

wherein the ratio of the number of moles of metal ions in the ionomer to the number of moles of the carboxylic acid or any anhydride thereof in the grafted EP, EPDM or styrenic thermoplastic elastomer is greater than or equal to 1.0.

BRIEF DESCRIPTION OF THE DRAWINGS

The figures are TEM images produced by cutting sections of molded bars or pellets perpendicular to the melt flow direction using a diamond knife. The sections were accumulated in cold ethanol, transferred to 1% phosphotungstic acid for overnight staining, rinsed, and captured on copper mesh grids. The images were recorded using a JEOP 1200 EX TEM operated at 100 KV accelerating voltage and recorded on sheet film. The scale of the image is evident from the micron bar shown on the image.

DEFINITIONS

The term "polymer" as used herein, generally includes but is not limited to, homopolymers, copolymers (such as for example, block, graft, random and alternating copolymers), terpolymers, etc. and blends and modifications thereof. Furthermore, unless otherwise specifically limited, the term "polymer" shall include all possible geometrical configurations of the material. These configurations include, but are not limited to isotactic, syndiotactic and random symmetries.

The term "EPDM" refers to ethylene propylene diene monomer elastomers and is used herein to mean any elastomer that is a terpolymer of ethylene, an alpha-olefin having from 3 to 10 carbon atoms, and a copolymerizable non-conjugated diene such as 5-ethylidene-2-norbornene, dicyclopentadiene, 1,4-hexadiene, and the like.

The term "EP" as used herein means any copolymer or terpolymer of ethylene and an alpha-olefin having from 3 to 10 carbon atoms, such as EPR, EPM, or an ethylene propylene copolymer.

DETAILED DESCRIPTION

The present invention relates to a multiphase polymer composition having increased impact resistance at low temperatures.

The inventive composition is a multiphase composition that includes a blend of (1) an ionomer at least partially dispersed in nylon 6, (2) a polyamide other than nylon 6, and (3) an EP or EPDM grafted with a carboxylic acid or any anhydride thereof, wherein the ratio of the number of moles of metal ions in the ionomer to the number of moles of the carboxylic acid or any anhydride thereof in the grafted EP or EPDM is greater than or equal to 1.0. The composition preferably includes from 10 to 50 weight percent nylon 6, from 1 to 30 weight percent of an ionomer of ethylene, methacrylic acid and maleic acid monoethyl ester, from 35 to 90 weight percent of a nylon other than nylon 6,6, and from 5 to 25 weight percent of EP or EPDM grafted with carboxylic acid or any anhydride thereof, based on the total weight of the composition.

Figure 2:
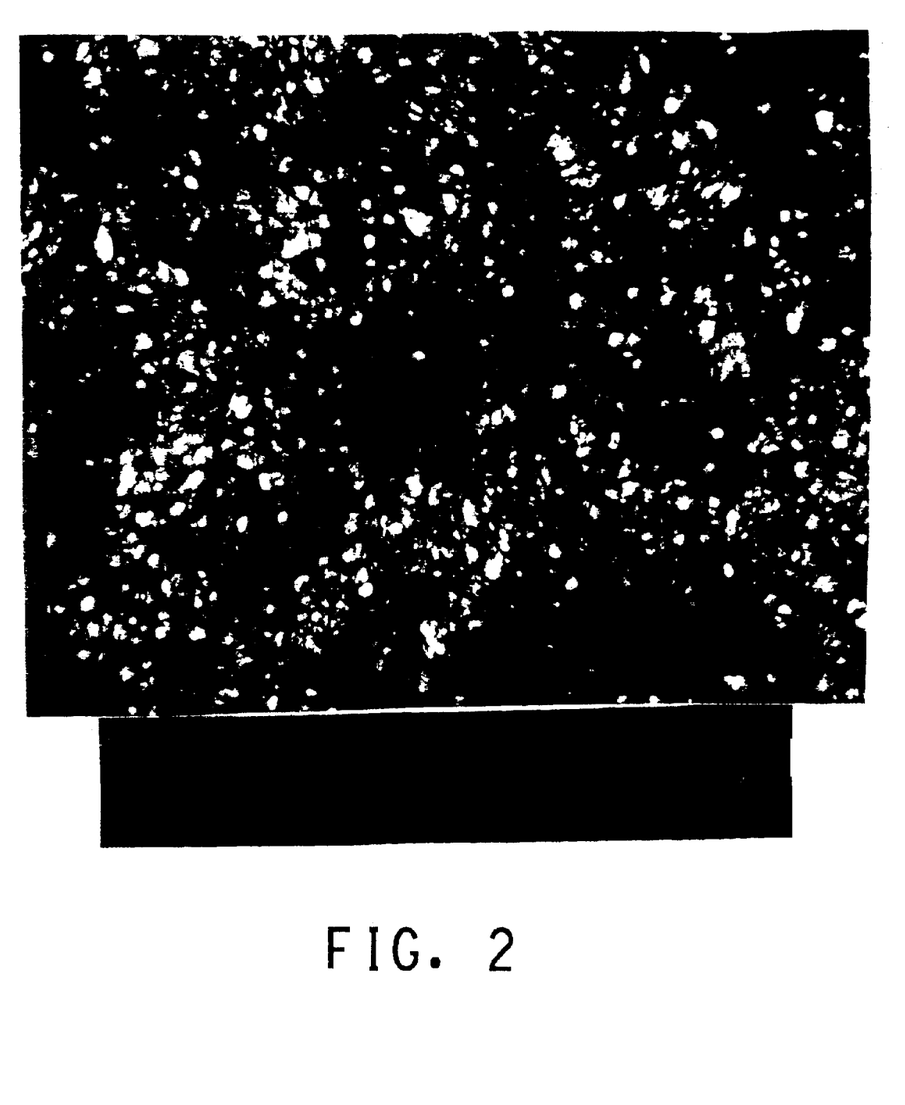
FIG. 2 is a TEM image of a composition nylon 6, a neutralized ionomer of ethylene, methacrylic acid and maleic acid monethyl ester, Nylon 6,6, and EP grafted with maleic anhydride.
Figure 3:
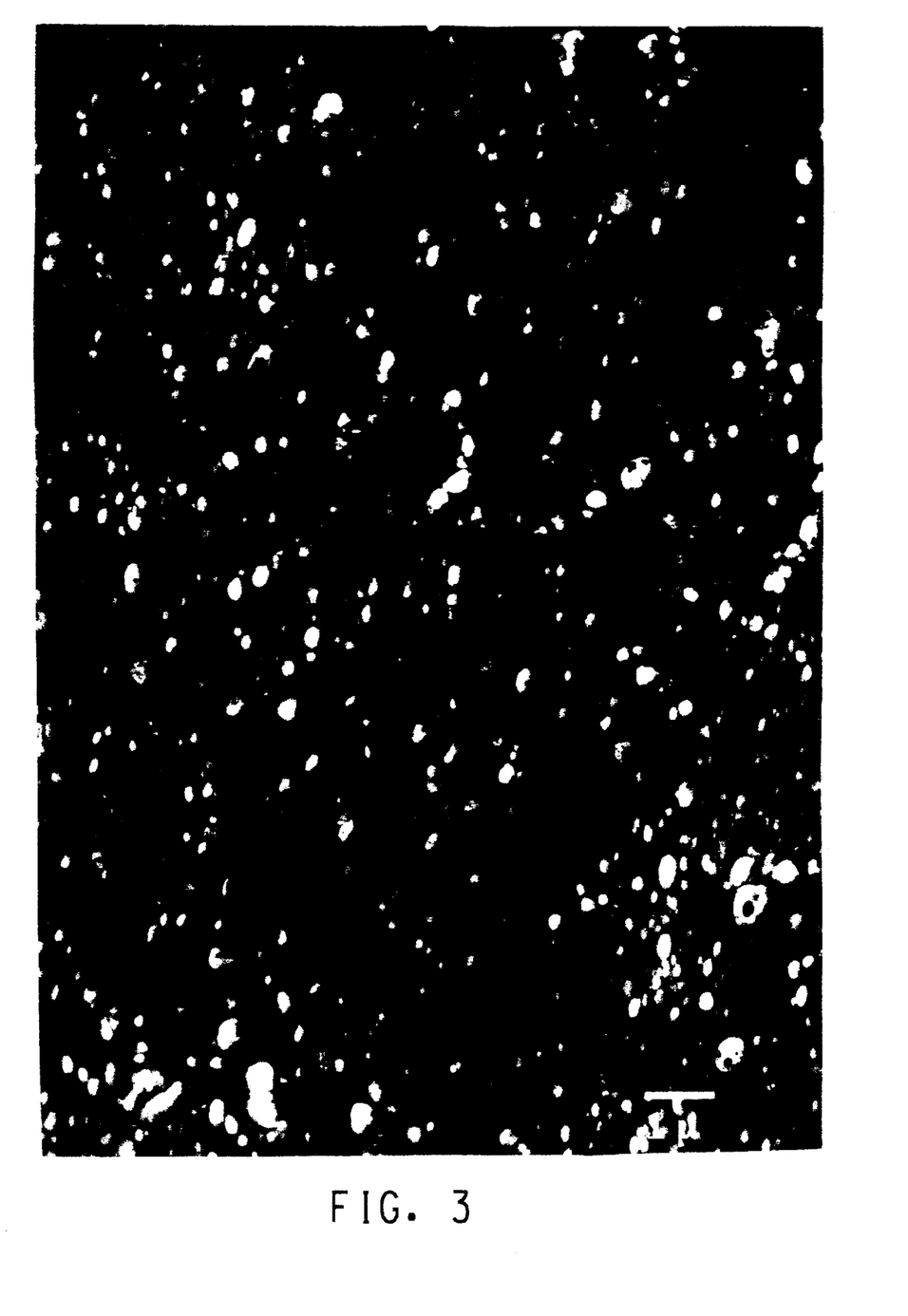
FIG. 3 is a TEM image of Zytel® ST801 NC01A impact modified nylon 6,6.

Without wishing to be bound by theory, it is believed that the composition of the invention enables a morphology that, when used in molded polyamide articles, is believed to result polyamide in articles that exhibit a significant increase in the ductility at low temperatures. With the composition of the invention, both a network of nylon in the elastomer and a network of elastomer in nylon is formed. As can be seen in FIG. 2, the morphology of an article made with a composition according to one preferred embodiment of the invention resembles interpenetrating polymer networks. The morphology of a molded article made with a conventional elastomer-toughened polyamide composition, as shown in FIG. 3, shows approximately spherical elastomer particles in a nylon matrix.

The ionomer of the composition of the invention is formed from a partially neutralized acid copolymer precursor (or the acid copolymer can be neutralized during dispersion), the acid copolymer precursor having polymerized in-chain units derived from the monomers comprising:

(a) ethylene, (b) 2 to 25 weight percent of an acid selected from the group of acrylic acid, methacrylic acid and mixtures thereof, (c) 0.1 to 15 weight percent of a dicarboxylic acid monomer selected from the group consisting of maleic acid, fumaric acid, itaconic acid, maleic anhydride, itaconic anhydride, a $C_1$–$C_4$-alkyl half ester of maleic acid, and a mixture of these dicarboxylic acid monomers, (d) 0–40 weight percent of a C1–C8-alkyl alkyl acrylate, the ionomer being formed by neutralization of from about 5 to 90 percent of the total number of carboxylic acid units in the copolymer with metal ions selected from the group of zinc, magnesium, manganese and mixtures thereof, alone or in combination with sodium or lithium ions (this neutralization level is the level prior to the compounding with the nylon 6).

Preferably, the total of (meth)acrylic acid and dicarboxylic acid monomer is from 4 to 26 weight percent of the acid copolymer precursor. It is further preferred that the total co-monomer content not exceed 50 weight percent of the acid copolymer precursor. The preferred ionomer has a melt index of from 0.01 to 100 grams/10 minutes.

This ionomer and its preparation are generally disclosed in International Application Number PCT/US98/03611, International Publication Number WO 98/38227, filed in the name of E.I. du Pont de Nemours and Company, the text of which is hereby incorporated by reference. For example, the precursor acid copolymers may also contain up to 40 weight percent of an alkyl arcyrlate having an alkylgroup with from 1 to 8 carbons. This is designated a C1–C8-alkyl arcrylate. If an alkyl acrylate is present, n-butyl is preferred In referring to percent neutralization of acid units of the ionomer, a monocarboxylic acid provides one acid unit, a dicarboxylic acid provides two acid units, an anhydride such as maleic anhydride is considered to provide two acid units, and half esters are considered to provide one acid unit. The calculation of percent neutralization is based on the number of acid units considered to be present as per above, and the number of metal equivalents added. In fact, anhydride units may remain as anhydride units rather than be changed to acid units. When subject to neutralization, an anhydride monomer unit may form a di-metal salt, a mono-metal salt, form an un-neutralized diacid unit, or leave the anhydride unit unaltered as an anhydride unit, acting as if it had no acid functionality. The half esters of diacids, while counted as having only one acid, may actually be converted to diacids or anhydrides, with the various possibilities related to neutralization noted above. The presence of water under pressure in the melt is one factor affecting these possibilities. As stated however, whatever the number of acid groups (free or neutralized) actually present, the calculated percent neutralization is based on the number of acid units considered to be provided as defined above. In view of the various 'mutations' of the diacid monomers and salts possible, the actual percent of neutralized acid groups as a percent of actual total neutralized and non-neutralized free acid groups may therefore differ from the calculated percent neutralization, which is based on the above assumptions. The difference is due to anhydride units which are not acid units, but are counted as two acid units.

The total percent neutralization, as defined in the above paragraphs, is from about 5 to 90 percent, preferably 10 to 70 percent, most preferably between 25 and 60 percent. While lower neutralization levels will provide less ionomer character, higher levels will produce lower flow ionomers.

The polyamide other than nylon 6 that is used in the composition of the invention may be nylon-6,6, nylon-6,10, nylon-6/66, nylon-6,12, nylon-12, nylon-11 or any high temperature nylon (polyphtalamide).

The grafted EP or EPDM is an EP or EPDM grafted with 0.05 to 3 weight percent of a carboxylic acid or any potential anhydride thereof. Preferably, the carboxylic acid or anhydride thereof is selected from the group consisting of maleic acid, fumaric acid, itaconic acid, maleic anhydride, itaconic anhydride, a $C_1$–$C_4$-alkyl half ester of maleic acid, and mixtures thereof. It is recognized that anhydride containing styrenic thermoplastic elastomers are functionally equivalent to the above grafted EP or EPDM elastomers.

The metal ions in the ionomer are selected from the group of zinc, magnesium, manganese and mixtures thereof, alone or in combination with sodium or lithium ions. A preferred metal ion is zinc.

The ratio of the number of moles of metal ions in the ionomer to the number of moles of the carboxylic acid or an anhydride thereof in the grafted EP or EPDM is greater than or equal to 1.0, and preferably greater than 1.5. There is no theoretical upper limit for this ratio, although a practical upper limit is 3.0. In addition to a kinetic limitation with regard to the percent of actual neutralization as opposed to the theoretically possible due to limited time in the mixing device, the reason for a practical upper limit is as follows. The ratio of the number of moles of metal ions in the ionomer to the number of moles of the carboxylic acid in the grafted EP or EPDM can be increased either by increasing the ionomer component or by decreasing the grafted EP or EPDM component. In the first case, when a large quantity of the ionomer in nylon 6 is used, it will leave only a small percentage of the nylon other than nylon 6 in which the grafted EP or EPDM has to dispersed. This would result in poor dispersion of the EP or EPDM. In the second case, where the grafted EP or EPDM is decreased, the reduced number of grafting sites will undesirably reduce the overall toughness of the material as it is known that low temperature impact resistance increases with concentration of grafting sites.

Without being bound to any particular theory, it is believed that the metal ions in the ionomer of the composition, and in particular the excess metal ions, interact with the some of the carboxylic acid or anhydride thereof that is grafted on the EP or EPDM. This interaction can be compared to the neutralization of the acid units of the ionomer by the metal ions as described above. In fact, the carboxylic acid or anhydride thereof grafted on the EP or EPDM can either react with the amine ends of the nylon or interact with the metal ions. It is believed that the interaction between the ionomer, the nylon 6, and the grafted EP or EPDM, when dispersed in the nylon other than nylon 6 generates a morphology which confers improved toughness and that looks like an interpenetrating network system.

The compositions of the present invention may be prepared by melt blending the ionomer and nylon 6, and then melt blending this composition with the polyamide other than nylon 6 and the EP or EPDM grafted with a carboxylic acid or anhydride thereof. The inventive composition may be made by admixing the components in the desired proportions and melt blending the admixture under high shear in conventional mixing equipment, such as an extruder, Banbury mill, Buss Kneader, Farrell Continuous Mixer or the like. The components are preferably combined with one another via simultaneous metering of the component streams. Pellet blends of the components can also be directly injection molded if sufficient mixing is present in the molding machine from back pressure, a mixing screw or head, static mixers in the die, or the like.

Blends prepared according to this invention may also contain one or more conventional additives, such as stabilizers and inhibitors of oxidative, thermal, and ultraviolet light degradation; lubricants and mold release agents; colorants including dyes and pigments; flame-retardants; fibrous and particulate fillers and reinforcements; plasticizers, processing aids, and the like. These additives are ordinarily added during the mixing step before melt blending or during melt blending.

The invention is further illustrated by the following examples. It will be appreciated that the examples are for illustrative purposes only and are not intended to limit the invention as described above. Modification of detail may be made without departing from the scope of the invention.

EXAMPLE 1

The composition of Examples 1A and 1B were made by blending nylon-6, an ionomer, nylon 6,6, and EP grafted with maleic anhydride.

The composition of Example 1A was made by forming a melt blend of the nylon-6 with the ionomer in a twin screw extruder and subsequently blending this first melt blend with the nylon 6,6 and the EP grafted with maleic anhydride in a twin screw extruder to form the complete composition.

Figure 1:
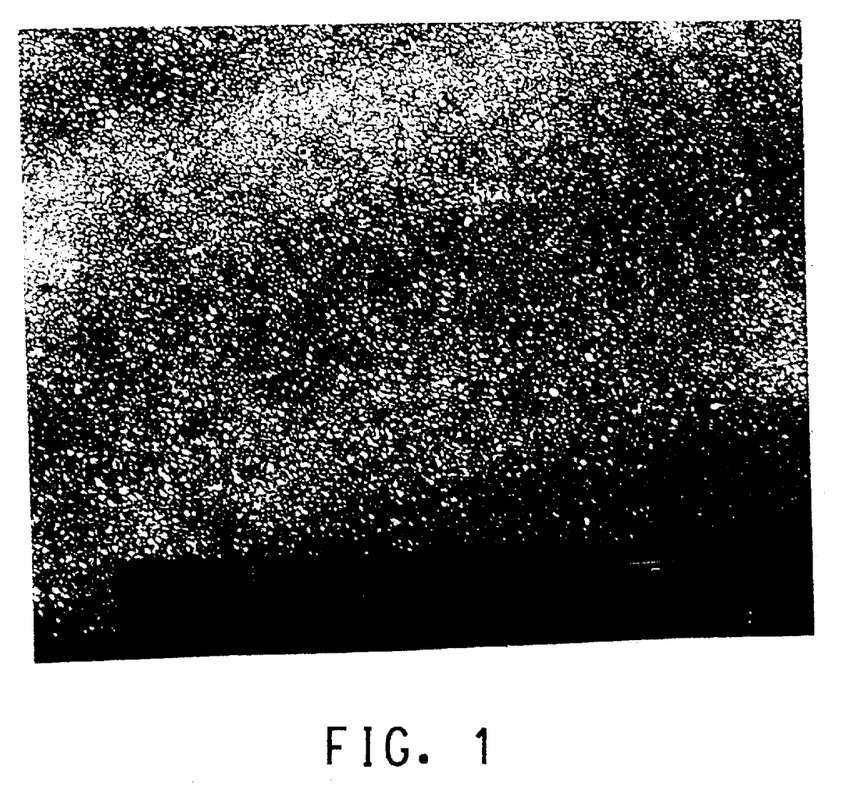
FIG. 1 is a TEM image of a composition of nylon 6 and a neutralized ionomer of ethylene, methacrylic acid and maleic acid monethyl ester.

The ionomer was a terpolymer of about 83 weight percent ethylene, 11 weight percent methacrylic acid, and 6 weight percent maleic acid monethyl ester having 40% neutralisation by Zinc, that was prepared as generally disclosed in International Application Number PCT/US98/03611. This ionomer was blended with nylon-6 (Viscosity Number ("VN") 131–153 in sulfuric acid, according to DIN 53727), at a ratio of 30 weight percent ionomer to 70 weight percent nylon-6, in a Berstorff twin screw extruder having a diameter of 40 mm and an L/D ratio of 33. The barrel temperature at set up was 270° C. at the hopper end and 240° C. towards the die end, and the die had a set-up temperature of 260° C. The screw was turned at 300 rpm and the two components were added to the extruder and combined via simultaneous addition to the extruder in a single pass. TEM images of this first blend (accumulated in cold ethanol and transferred to 1% phosphotungstic acid) showed a very evenly-sized dispersion of approximately spherical elastomer particles with an average particle size of 0.014 to 0.07 μm. A TEM image of this blend is shown in FIG. 1.

The complete composition of Example 1A was formed by melt blending 26 weight percent of the first blend described above with 55 weight percent nylon 6,6 (VN 138 to 149 in Formic acid, according to ISO307) and with 19 weight percent EP grafted with maleic anhydride (MFI 20@280°C., 2.16 Kg; 0.9% MAh). This complete composition was blended according to the same process conditions used to produce the first blend except that the barrel temperature at set up was 300° C. at the hopper end and 270° C. towards the die end, and the die had a set-up temperature of 280° C. The ratio of the moles of zinc to moles of maleic anhydride in this complete composition was 1.5, which is calculated by taking the number of moles of zinc in the ionomer and dividing that by the number of moles of maleic anhydride grafted onto the EP. As used herein, the percent neutralization is equal to this ratio multiplied by 100.

In Example 1B, the nylon-6 (VN 131–153 in sulfuric acid, according to DIN 53727) and the ionomer of Example 1A were directly dry-blended with the nylon 6,6 and the EP grafted with maleic anhydride in a twin screw extruder at the following ratio to form the complete composition: 18.2 weight percent of nylon-6, 7.8 weight percent of the ionomer, 55 weight percent nylon 6,6, and 19 weight percent EP grafted with maleic anhydride. The complete composition of Example 1B was blended under the same process conditions that were used to produce the complete composition of Example 1A.

Test flex bars (5 to 10 bars per example per test) of the inventive composition, blended according to the processes of Examples 1A and 1B, were molded according to ISO 294 in a standard injection molding machine with a melt temperature of about 285° C., a mold temperature of about 75° C., and a hold pressure of 85 MPa. The molded flex bars were notched according to specimen type 1A in ISO 180 and were tested according to the Notched Izod (NI) test method ISO 180 at 23° C. in the dry-as-molded state (DAM) and in the 50% relative humidity conditioned state (50% RH). Flex bars in the DAM state were notched and tested according to the same test methods at −30° C. and −40° C. The average impact energy measurements as per ISO 180 are reported in units of KJ/m$^2$ in Table 1.

TABLE 1

|  | Example 1A (Melt pre-blend) | Example 1B (Dry-blend) |
| --- | --- | --- |
| Notched Izod 23° C. DAM | 89 | 90 |
| Notched Izod 23° C. 50% RH | 95 | 89 |
| Notched Izod −30° C. DAM | 75 | 77.4 |
| Notched Izod −40° C. DAM | 36.6 | 37.5 |

The test results in Table 1 show that the composition of this invention can be prepared by pre-blending the nylon-6 with the ionomer and subsequently blending this first blend with the nylon 6,6 and the EP grafted with maleic anhydride, or it can be prepared by directly dry-blending nylon-6 and the ionomer with the nylon 6,6 and the EP grafted with maleic anhydride without significantly changing the ductility of the material. TEM images of samples in Table 1 (accumulated in cold ethanol and transferred to 1% phosphotungstic acid) showed a morphology which looks like interpenetrating networks (IPN) with an average particle size of 0.04 to 0.3 m. A TEM image of the composition of Example 1A is shown in FIG. 2.

COMPARATIVE EXAMPLE 2

In Comparative Example 2, molded flex bars consisting 100% of the commercially available impact modified nylon 6,6 product Zytel® ST801 NC01A, available from E.I du Pont de Nemours and Company, Wilmington, Del., were tested for impact resistance. The test flex bars (5 to 10 bars per test) were molded according to ISO 294 in a standard injection molding machine with a melt temperature of about 285° C., a mold temperature of about 75° C., and a hold pressure was 85 MPa.

The molded flex bars as described above were notched according to specimen type 1A in ISO 180 and tested in the dry-as-molded state according to the Notched Izod test used in Example 1 at 23° C., −30° C. and −40° C. The average impact energy measurements as per ISO 180 are reported in units of KJ/m$^2$ in Table 2.

TABLE 2

|  | Comp. Example 2 (ST801 NC101A) | EXAMPLE 1A (melt pre-blend) | Example 1B (dry-blend) |
| --- | --- | --- | --- |
| Notched Izod 23° C. DAM | 85 | 89.0 | 90.0 |
| Notched Izod −30° C. DAM | 23 | 75 | 77.4 |
| Notched Izod −40° C. DAM | 19 | 36.6 | 37.5 |

The results in Table 2 show that at low temperatures, the composition of the invention (Example 1) provides a further improvement in ductility over a well known and commercially available impact modified polyamide composition, as represented by an increase in Notched Izod of more than 300% at −30° C. compared to the compositions of the Zytel® ST801 NC01A at −30° C., dry as molded. FIG. 3 shows a TEM image of Zytel® ST801 NC010A (accumulated in cold ethanol and transferred to 1% phosphotungstic acid) in which nearly spherical elastomer particles of average particle size between 0.04 and 0.9 μm dispersed in the nylon matrix can be seen.

EXAMPLE 3

Compositions were made according to the process of Example 1A except that the relative weight percents of the nylon-6, the ionomer, and the nylon 6,6 were varied as shown in Table 3 to change the level of neutralization. Molded flex bars comprised of the compositions 3A, 3B and 3C, were tested for impact resistance according to the Notched Izod test method used in Example 1. The test flex bars (5 to 10 bars per test) were molded according to ISO 294 in a standard injection molding machine with a melt temperature of about 285° C., a mold temperature of about 75° C., and a hold pressure was 85 MPa. The bars were tested in the dry-as-molded state at 23° C., −30° C. and −40° C. The average impact energy measurements as per ISO 180 for Examples 3A, 3B and 3C, as well as for Example 1A are reported in units of KJ/m$^2$ in Table 3

TABLE 3

| Example | 3A | 3B | 1A | 3C |
| --- | --- | --- | --- | --- |
| Composition (weight %) | | | | |
| Nylon 6 | 6.1 | 12.3 | 18.2 | 24.5 |
| Ionomer | 2.6 | 5.2 | 7.8 | 10.5 |
| Nylon 6,6 | 72.3 | 63.5 | 55 | 46 |
| g-Mah-EP | 19 | 19 | 19 | 19 |

TABLE 3-continued

| Example | 3A | 3B | 1A | 3C |
|---|---|---|---|---|
| % Neutralization | 50 | 100 | 150 | 200 |
| Properties | | | | |
| Notched Izod 23° C. DAM | 85.2 | 82.3 | 89.0 | 92.9 |
| Notched Izod −30° C. DAM | 24.6 | 67.5 | 75 | 82.1 |
| Notched Izod −40° C. DAM | 17.6 | 31.7 | 36.6 | 41.5 |

The results in Table 3 show that a level of neutralization of about 100% is desired to achieve the desired improvement in ductility at −30° C. A preferred level of neutralization that achieves superior impact resistance at −30° C. is 150%.

EXAMPLE 4

Compositions were made according to the process of Example 1A except that the total elastomer modifier level was varied, at two neutralization levels, namely at 50% and 150%. The total elastomer modifier level was the combined weight percent of the ionomer of Example 1 and the maleic anhydride-grafted EP (MFI 20@280° C., 2.16 Kg; 0.9% MAh). The level of maleic anhydride was also varied within each level of neutralization. Molded flex bars comprised of the compositions 4A, 4B and 4C were tested for impact resistance according to the Notched Izod test method used in Example 1. The test flex bars (5 to 10 bars per test) were molded according to ISO 294 in a standard injection molding machine with a melt temperature of about 285° C., a mold temperature of about 75° C., and a hold pressure was 85 MPa. The bars were tested in the dry-as-molded state at 23° C., −30° C. and −40° C. The average impact energy measurements as per ISO 180 are reported in units of KJ/m² in Table 4 and are compared against Examples 1A and 3C.

TABLE 4

| Example | 4A | 4B | 4C | 1A | 3B |
|---|---|---|---|---|---|
| Composition (weight %) | | | | | |
| Nylon 6 | 3.1 | 6.1 | 9.1 | 18.2 | 12.3 |
| Ionomer | 1.3 | 2.6 | 3.9 | 7.8 | 5.2 |
| Nylon 6,6 | 86.1 | 72.3 | 77.5 | 55.0 | 63.5 |
| g-Mah-EP | 9.5 | 19.0 | 9.5 | 19.0 | 19.0 |
| Total elastomer % | 10.8 | 21.6 | 13.4 | 26.8 | 24.2 |
| % Neutralisation | 50 | 50 | 150 | 150 | 100 |
| Properties | | | | | |
| Notched Izod 23° C. DAM | 21.8 | 85.2 | 57.5 | 89 | 82.3 |
| Notched Izod −30° C. DAM | 12.2 | 24.6 | 16.4 | 75 | 67.5 |
| Notched Izod, −40° C. DAM | 12.3 | 17.6 | 14.4 | 36.6 | 31.7 |

The results in Table 4 suggest that even when the total elastomer level is high, a substantial improvement in ductility is achieved at −30° C. only at a high neutralization level (Examples 1A and 3B).

EXAMPLE 5

A composition was made according to the process of Example 1A except that the composition of the elastomer phase was varied. A different maleic anhydride-grafted EP was used so as to keep the level of maleic anhydride contributed by the maleic anhydride-grafted EP the same as in Example 1A while varying the level of total elastomer. In Example 1A, the maleic anhydride-grafted EP was 0.9% MAh and with an MFI of 20@280° C., 2.16 Kg. In Example 5, the maleic anhydride-grafted EP was 2% MAh with an MFI of 1@190° C., 2.16 Kg. The percent of neutralization was maintained at 150% in Example 5.

Molded flex bars comprised of the composition of Example 5 were tested for impact resistance according to the Notched Izod test method used in Example 1. The test flex bars (5 to 10 bars per test) were molded according to ISO 294 in a standard injection molding machine with a melt temperature of about 285° C., a mold temperature of about 75° C., and a hold pressure was 85 MPa. The bars were tested in the dry-as-molded state at 23° C., −30° C. and −40° C. The average impact energy measurements as per ISO 180 are reported in units of KJ/m² in Table 5 and are compared against the results of Example 1A.

TABLE 5

| Example | 1A | 5 |
|---|---|---|
| Composition (weight %) | | |
| Nylon 6 | 18.2 | 18.2 |
| Ionomer | 7.8 | 7.8 |
| Nylon 6,6 | 55.0 | 64.0 |
| g-Mah-EP | 19.0 | 10.0 |
| Total elastomer % | 26.8 | 17.8 |
| Properties | | |
| Notched Izod 23° C. DAM | 89.0 | 88.4 |
| Notched Izod −30° C. DAM | 75.0 | 30.7 |
| Notched Izod, −40° C. DAM | 36.6 | 24.6 |

The results in Table 5 suggest that at the same level of neutralization, and even at the same level of maleic anhydride contributed by the maleic anhydride-grafted EP, the total level of elastomer contributes to the substantial increase in ductility at −30° C.

EXAMPLE 6

Compositions were made according to the process of Example 1 except that the nature of the nylon feedstock was varied. In Example 6A, the ionomer of Example 1, the EP grafted with maleic anhydride, and nylon 6,6 (VN 138 to 149 in formic acid, according to ISO 307) were melt blended according to the process used in Example 1B. In Example 6B, the ionomer of Example 1, EP grafted with maleic anhydride, and nylon 6 (VN 131–153 in sulfuric acid, according to DIN 53727) were melt blended according to the process used in Example 1B. These compositions were compared against the composition of Example 1A in which the ionomer, nylon 6 (VN 131–153 in sulfuric acid, according to DIN 53727), EP grafted with maleic anhydride, and nylon 6,6 (VN 138 to 149 in formic acid, according to ISO 307) were blended. In Examples 6A, 6B and 1A, the EP was grafted with 0.9% maleic anhydride and it had an MFI of 20@280° C., 2.16 Kg.

Molded flex bars comprised of the compositions 6A and 6B were tested for impact resistance according to the Notched Izod test method used in Example 1. The test flex bars (5 to 10 bars per test) were molded according to ISO 294 in a standard injection molding machine with a melt temperature of about 285° C., a mold temperature of about 75° C., and a hold pressure was 85 MPa. The bars were tested in the dry-as-molded state at 23° C., −30° C. and −40° C. In Table 6, the average impact energy measurements as per ISO 180 are reported in units of KJ/m² for Examples 6A and 6B and for Example 1A.

TABLE 6

| Example | 6A | 6B | 1A |
|---|---|---|---|
| Composition (weight %) | | | |
| Nylon 6 | 0 | 73.2 | 18.2 |
| Ionomer | 7.8 | 7.8 | 7.8 |
| Nylon 6,6 | 73.2 | 0 | 55.0 |
| g-MAh-EP | 19.0 | 19.0 | 19.0 |
| Properties | | | |
| Notched Izod 23° C. DAM | 85.1 | 20 | 89 |
| Notched Izod −30° C. DAM | 29.8 | 19 | 75 |
| Notched Izod, −40° C. DAM | 23.7 | 17 | 36.6 |

Figure 4:
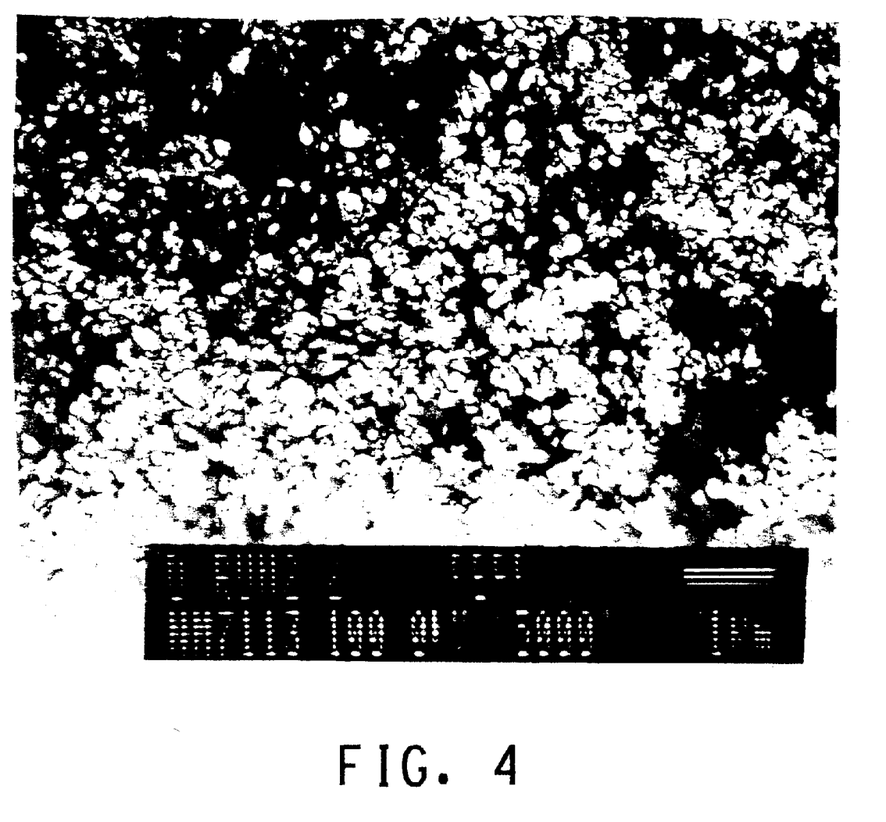
FIG. 4 is a TEM image of a composition a neutralized ionomer of ethylene, methacrylic acid and maleic acid monethyl ester, nylon 6,6, and EP grafted with maleic anhydride.
Figure 5:
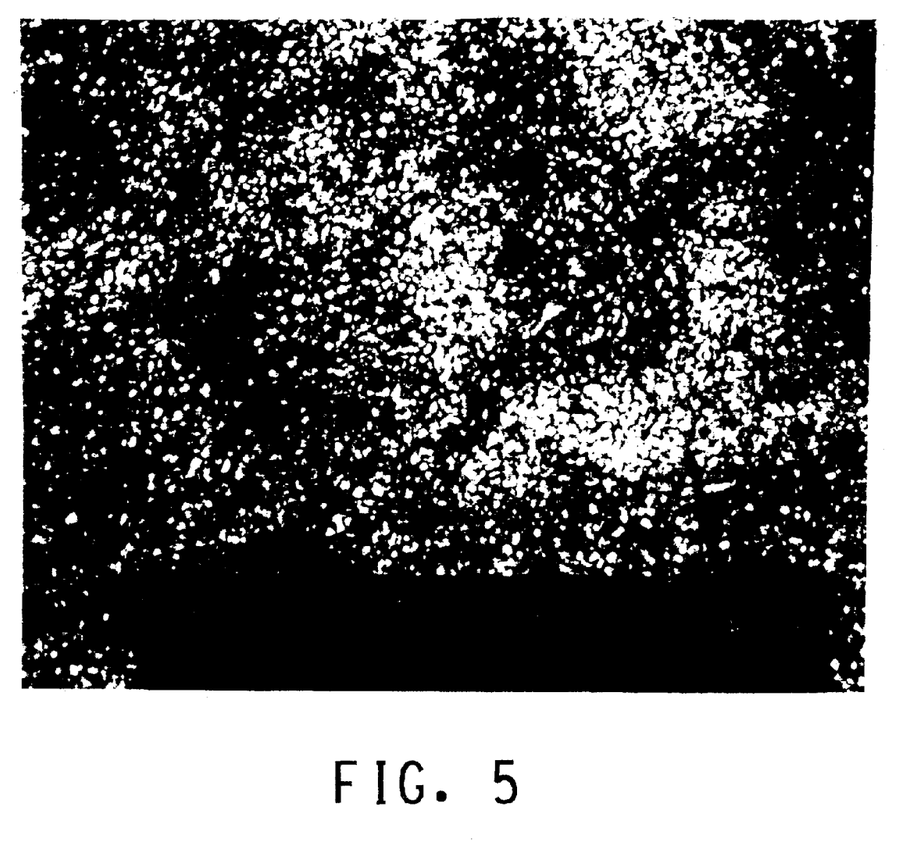
FIG. 5 is a TEM image of a composition nylon 6, a neutralized ionomer of ethylene, methacrylic acid and maleic acid monethyl ester, and EP grafted with maleic anhydride.

The results in Table 6 show that a substantial increase in ductility, measured according to the Notched Izod, is achieved at −30° C. only when the feedstock is a mixture of nylon 6 and nylon 6,6. A TEM image of the composition of Example 6B, as shown in FIG. 5, where only nylon 6 was included in the composition, shows a quasi-monodisperse morphology (very similar to that of the blend shown in FIG. 1) with a particle size range between 0.02 and 0.2 μm. A TEM image of the composition of Example 6A (FIG. 4), where only nylon 6,6 was included in the composition, shows a morphology which looks like interpenetrating networks similar to the composition shown in FIG. 2, with average particle size between 0.02 and 0.3 μm. However, it was only when both nylon 6 and nylon 6,6 were present in the composition that a morphology was obtained that looks like interpenetrating networks and that the substantial improvement in ductility at −30° C. was achieved.

What is claimed is:

1. A multiphase polymer composition having increased impact resistance at low temperatures, said composition comprising a blend of
   (1) an ionomer at least partially dispersed in nylon 6, said ionomer being formed from a partially neutralized acid ethylene acid interpolymer, said acid interpolymer having polymerized in-chain units derived from the monomers comprising:
      (a) ethylene,
      (b) 2 to 25 weight percent of an acid selected from the group of acrylic acid, methacrylic acid, and mixtures thereof,
      (c) 0.1 to 15 weight percent of a dicarboxylic acid monomer selected from the group consisting of maleic acid, fumaric acid, itaconic acid, maleic anhydride, itaconic anhydride, a $C_1$–$C_4$-alkyl half ester of maleic acid, and a mixture of these dicarboxylic acid monomers,
      (d) 0–40 weight percent of a C1–C8-alkyl alkyl acrylate,
   the ionomer being formed by neutralization of from about 5 to 90 percent of the total number of carboxylic acid units in the copolymer with metal ions, with the proviso that the total of acrylic acid, methacrylic acid and dicarboxylic monomer is from 4 to 26 weight percent of the acid interpolymer, and with the further proviso that at least 50 weight percent of the acid interpolymer consists of ethylene, the ionomer having a melt index of from 0.01 to 100 grams/10 minutes;
   (2) a polyamide other than nylon 6
   (3) composition that includes an elastomer selected from the group of EP, EPDM and styrenic thermoplastic elastomer, which elastomer is grafted with 0.05 to 3 weight percent of a carboxylic acid or any anhydride thereof;
   wherein the ratio of the number of moles of metal ions in the ionomer to the number of moles of the carboxylic acid in the grafted EP, EPDM or styrenic thermoplastic elastomer is at least 1.0.

2. The composition of claim 1 where component (1) can be made by melt-blending or dry-blending of the ionomer and nylon 6.

3. The composition of claim 1, wherein the elastomer portion represents more than 20% based on the total weight of the formulation.

4. The composition of claim 1, wherein the ionomer is formed by neutralization of from about 10 to 70 percent of the total number of carboxylic acid units in the copolymer with a metal ion.

5. The composition of claim 1 wherein the metal ion is selected from the group of zinc, magnesium, manganese and mixtures thereof, alone or in combination with other metal cations.

6. The composition of claim 5 wherein the metal cations are selected from the group of sodium, potassium, or lithium.

7. The composition of claim 1, wherein the polyamides in component (2) are aliphatic or partially aliphatic nylons.

8. The composition of claim 7, wherein the polyamide of component (2) is nylon 6,6.

9. The composition of claim 1, wherein component (3) contains an EP or EPDM grafted with a carboxylic acid or an anhydride precursor selected from the group consisting of maleic acid, fumaric acid, itaconic acid, maleic anhydride, itaconic anhydride, a $C_1$–$C_4$-alkyl half ester of maleic acid, and mixtures thereof.

10. The composition of claim 1, wherein the ratio of the number of moles of metal ions in the ionomer to the number of moles of the carboxylic acid or any anhydride precursor in the grafted EP or EPDM is at least 1.0.

11. The composition of claim 10, wherein the ratio of the number of moles of metal ions in the ionomer to the number of moles of the carboxylic acid or any anhydride precursor in the grafted EP or EPDM is at least 1.5.

12. The composition of claim 1, wherein the elastomer of component (3) is EP grafted with maleic anhydride.

13. A molded article made from any of the compositions of claims 1 to 8.

* * * * *